United States Patent [19]

Serdar et al.

[11] Patent Number: 5,173,425
[45] Date of Patent: Dec. 22, 1992

[54] ENHANCEMENT OF NAPHTHALENE DIOXYGENASE ACTIVITY DURING MICROBIAL INDIGO PRODUCTION

[75] Inventors: Cuneyt M. Serdar, Newbury Park; Douglas C. Murdock; Burt D. Ensley, Jr., both of Thousand Oaks, all of Calif.

[73] Assignee: Amgen Inc., Thousand Oaks, Calif.

[21] Appl. No.: 289,738

[22] Filed: Aug. 4, 1989

[51] Int. Cl.⁵ .................. C12N 1/20; C12N 9/02; C12N 15/00; C07K 13/00
[52] U.S. Cl. .................. 435/252.3; 435/189; 435/172.1; 435/320.1; 536/27; 935/10; 935/14; 530/400
[58] Field of Search ........... 530/400; 435/189, 320.1, 435/252.3, 190 T, 172.3; 935/42; 536/27

[56] References Cited

U.S. PATENT DOCUMENTS 4,520,103  5/1985  Ensley, Jr. .................. 435/121

FOREIGN PATENT DOCUMENTS 8401787  5/1984  PCT Int'l Appl. .

OTHER PUBLICATIONS

Ensley et al., "Napthalene Dioxygenase: Purification and Properties . . . ", *J. Bact.* Aug. 1983, vol. 155, No. 2, pp. 505-511.
Kurkela et al., "Cloning, Nucleotide Sequence and Characterization of Genes Encoding Napthalene Dioxygenase . . . ", *Gene*, 73 (1988) 355-362.
Ensley, B. D., et al., "Expression of Naphthalene Oxidation Genes in *Escherichia coli* Results in the Biosynthesis of Indigo", *Science*, vol. 222, Oct. 14, 1983, pp. 167-169.
Ensley, B. D., et al., "Expression and Complementation of Napthalene Dioxygnase Activity in *Escherichia coli*", *Microbial Metabolism and the Carbon Cycle:* A symposium in honor of Stanley Dagley, Jul. 13-16, 1987, Hagedorn, et al., ed., pp. 437-455.
Ensley, B. D. and D. T. Gibson, "Napthalene Dioxygenase: Purification and Properties of a Terminal Oxygenase Component", *Journal of Bacteriology*, Aug. 1983, vol. 155, No. 2, pp. 505-511.
Ensley, B. D., et al., "Oxidation of Naphthalene by a Multicomponent Enzyme System from *Pseudomonas* sp. Strain NCIB 9816", *Journal of Bacteriology*, Mar. 1982, vol. 149, No. 3, pp. 948-954.
Yen, K. M. and I. C. Gunsalus, "Plasmid gene organization: Napthalene/salicylate oxidation", *Proc. Natl. Acad. Sci. USA*, Feb. 1982, vol. 79, pp. 874-878.

*Primary Examiner*—Robert A. Wax
*Assistant Examiner*—Keith D. Hendricks
*Attorney, Agent, or Firm*—Marshall, O'Toole, Gerstein, Murray & Bicknell

[57] ABSTRACT

This invention relates to a process for the enhancement of naphthalene dioxygenase activity in organisms that have been transformed with DNA encoding the expression of a multiple component naphthalene dioxygenase enzyme. Cells containing the naphthalene dioxygenase enzyme are capable of producing indigo when cultured in the presence of indole. The invention includes procedures to enhance naphthalene dioxygenase activity by transforming a host cell with a DNA sequence that encodes at least two ferredoxin polypeptides for each reductase polypeptide and iron-sulfur polypeptide, by growing transformed organisms in the presence of iron, or by transforming a host cell with a DNA sequence that encodes a ferredoxin analog.

17 Claims, 2 Drawing Sheets

FIG. 4 pN1816
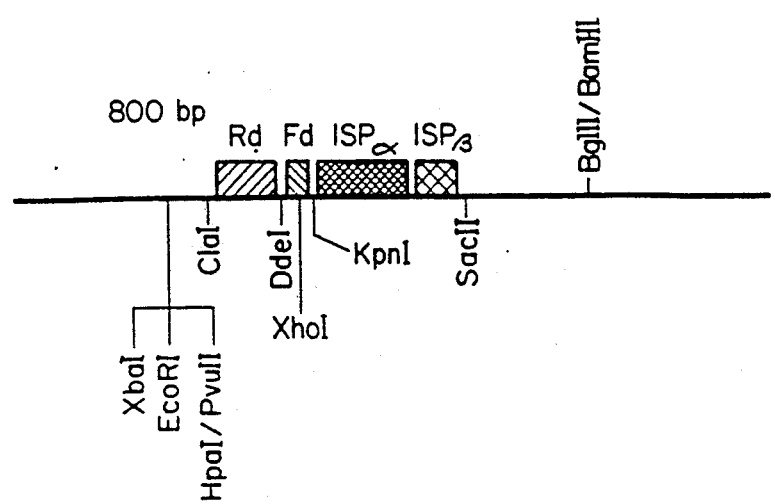
FIG. 5 Pro R/Sac
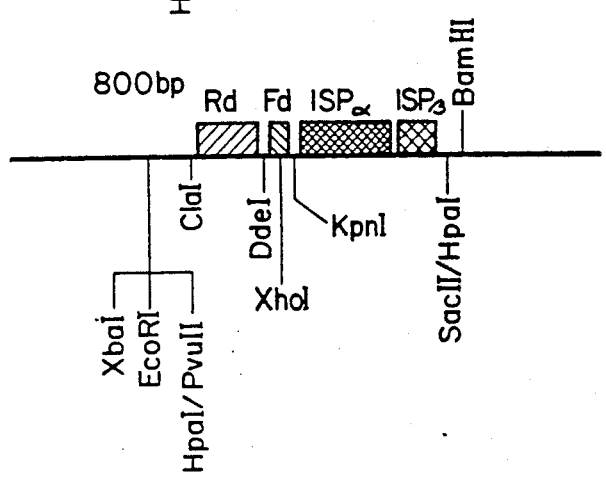
FIG. 6 911-pAC1
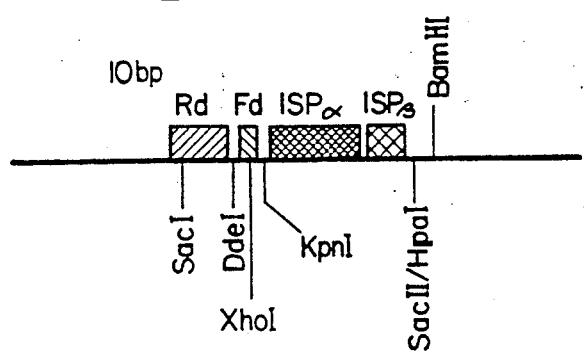
FIG. 7 IFd-911
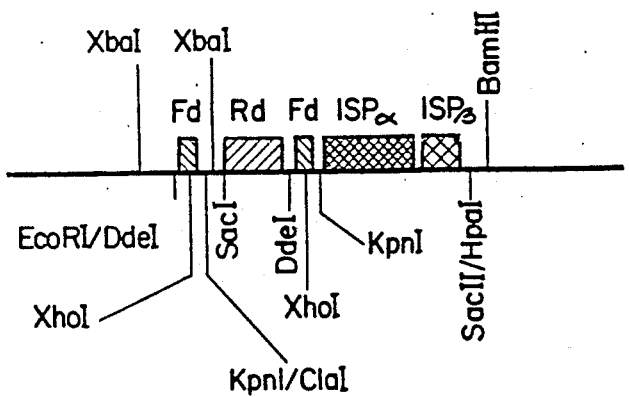

ENHANCEMENT OF NAPHTHALENE DIOXYGENASE ACTIVITY DURING MICROBIAL INDIGO PRODUCTION

BACKGROUND OF THE INVENTION

The present invention encompasses a process for the enhancement of naphthalene dioxygenase activity in organisms that have been stably transformed with a DNA sequence encoding a multiple component naphthalene dioxygenase enzyme. In particular, the enhancement of naphthalene dioxygenase activity is evident in a microbe transformed with multiple copies of the ferredoxin gene, in a microbe cultured in the presence of iron, and in a microbe transformed with a site specifically mutated ferredoxin gene.

Indigo, or indigotin, occurs as a glucoside in many plants of Asia, the East Indies, Africa, and South America, and has been used throughout history to dye textiles with a lasting navy blue color. Before elucidation of the structure and the synthetic production of this compound, natural indigo was liberated from plants by protracted fermentation processes and then introduced into fabric as a soluble, colorless glycosylated derivative called indican. The soluble indican was easily hydrolyzed to glucose and indoxyl and, upon exposure to air, the indoxyl would oxidize to indigo, generating the dark blue pigment in the fibers of the fabric.

The chemical structure of indigo was deduced in 1883 and a commercially feasible manufacturing process was developed about 1887. All known successful industrial processes involve the air oxidation of indoxyl to indigo.

U.S. Pat. No. 4,520,103 to Ensley describes a process for transforming $E.$ $coli$ with a DNA expression vector that contains a gene for the expression of the multiple component enzyme, naphthalene dioxygenase, (NDO). The presence of this enzyme in $E.$ $coli$ results in the ability of the microbe to synthesize indigo when the cells are cultured in the presence of a source of indole. Ensley et al., Science, 222:167 (1983) proposes that in the NDO-mediated indole to indigo biosynthesis, cis-indole-2,3-dihydrodiol and indoxyl are likely intermediates.

SUMMARY OF THE INVENTION

The present invention relates to the enhancement of NDO activity during indigo formation by recombinant microorganisms. According to this invention, the NDO activity during microbial indigo production may be enhanced using the following three processes or any combination of the three processes.

One process for enhancing NDO activity in an organism having DNA sequences that express a naphthalene dioxygenase enzyme which comprises reductase, ferredoxin and iron-sulfur polypeptides, comprises the step of transforming the organism with a DNA sequence encoding at least two ferredoxin polypeptides for each reductase and iron-sulfur polypeptide. The DNA sequence encoding at least two ferredoxin polypeptides for each reductase polypeptide is also within the scope of this invention.

Another process for enhancing NDO activity in an organism having DNA sequences that express a naphthalene dioxygenase enzyme which comprises reductase, ferredoxin and iron-sulfur polypeptides, comprises the step of growing the organism in a culture broth containing an amount of iron effective to enhance the NDO activity. Preferably, an effective amount of iron is from about 1.8 to 3.6 g/l of $FeSO_4.7H_2O$.

A third process for enhancing NDO activity in an organism having DNA sequences that express a naphthalene dioxygenase enzyme which comprises reductase, ferredoxin and iron-sulfur polypeptides comprises the step of transforming the organism with a DNA sequence encoding a ferredoxin analog. Preferably, the ferredoxin analog DNA sequence encodes Cys at position 47, Ile at position 52 and Arg at position 67 of the ferredoxin amino acid sequence. The DNA sequence encoding the ferredoxin analog and ferredoxin analog amino acid sequence are also within the scope of this invention.

A preferred combination of the three processes described above includes transforming an organism, having DNA sequences that express a naphthalene dioxygenase enzyme which comprises reductase, ferredoxin and iron-sulfur polypeptides, with a DNA sequence encoding at least two ferredoxin polypeptides for each reductase polypeptide and iron-sulfur polypeptide and growing the transformed organism in a culture broth containing an amount of iron effective to enhance the NDO activity.

Another preferred combination of processes includes transforming an organism, having DNA sequences that express a naphthalene dioxygenase enzyme which comprises reductase, ferredoxin and iron-sulfur polypeptides, with a DNA sequence encoding a ferredoxin analog and growing the transformed organism in a culture broth containing an amount of iron effective to enhance the NDO activity.

A third preferred combination of processes includes transforming an organism, having DNA sequences that express a naphthalene dioxygenase enzyme which comprises reductase, ferredoxin and iron-sulfur polypeptides, with a DNA sequence encoding at least two ferredoxin polypeptides for each reductase polypeptide and iron-sulfur polypeptide, where the DNA sequence encodes a ferredoxin analog and growing the transformed organism in a culture broth containing an amount of iron effective to enhance the NDO activity.

The present invention also encompasses a plasmid comprising a DNA sequence encoding a ferredoxin analog. Preferably, the ferredoxin analog DNA sequence encodes Cys at position 47, Ile at position 52 and Arg at position 67 of the ferredoxin analog amino acid sequence. The presently preferred plasmids are Fd-911ABC and Fd-pAC1ABC. Host cells containing these plasmids are also within the scope of the invention.

Another plasmid encompassed by this invention comprises a DNA sequence encoding at least two ferredoxin polypeptides for each reductase polypeptide and the iron-sulfur polypeptide. Preferably, the plasmid is Fd-911. Host cells containing these plasmids are also within the intended scope of the invention.

Other aspects and advantages of the present invention will be apparent upon consideration of the following description of the drawings and detailed description which includes several illustrative examples of the practice of the invention.

BRIEF DESCRIPTION OF THE DRAWINGS

FIG. 4 is a schematic illustration of construct PN1816;

FIG. 5 is a schematic illustration of construct Pro R/Sac;

FIG. 6 is a schematic illustration of construct 911-pACl; and

FIG. 7 is a schematic illustration of construct Fd-911.

DETAILED DESCRIPTION OF THE INVENTION

Figure 1:
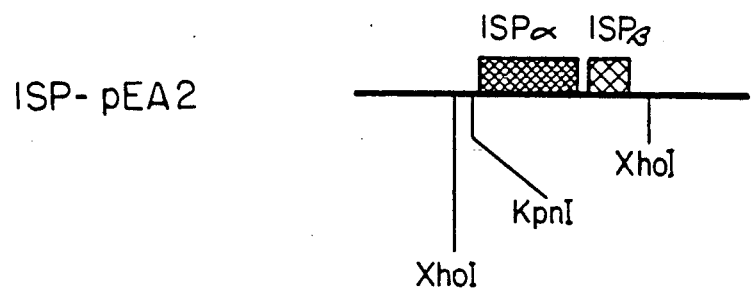
FIG. 1 is a schematic illustration of construct ISP-pEA2.

The NDO enzyme consists of three polypeptides: a reductase polypeptide (Rd, molecular weight about 37,000), an iron-sulfur ferredoxin polypeptide (Fd, molecular weight about 13,000) and a terminal oxygenase iron-sulfur protein (ISP) that contains two subunits with an $\alpha_2\beta_2$ subunit structure (molecular weights: $\alpha$ about 55,000, $\beta$ about 21,000). In substrate binding studies, ISP binds to naphthalene and the reduction of this enzyme-substrate complex by NADH in the presence of Rd, Fd and oxygen results in the conversion of ISP-bound naphthalene to cis-naphthalene dihydrodiol.

The naphthalene oxidation limiting polypeptide was identified by adding the cell extract from cells expressing only one polypeptide encoded by a single NDO gene to the cell extract of a cell expressing all three polypeptides. Three plasmids, each containing an isolated gene encoding one of three polypeptides of the NDO enzyme, were constructed. The constructions of the three plasmids, were done using recombinant techniques known to those skilled in the art.

General methods used in the isolation of DNA, the cleavage of DNA with restriction enzymes, the construction of recombinant plasmids and the introduction of the recombinant plasmids into microbial host cells are known in the art and are described in many publications including Maniatis et al., *Molecular Cloning—A Laboratory Manual*, Cold Spring Harbor Laboratory, chapters 3, 4, 5, 8, 11 and 12 (1982) and *Current Protocols in Molecular Biology*, edited by Ausubel et al., Greene Publishing Associates and Wiley Interscience, chapters 1, 2 and 3 (1987). All DNA modifying enzymes used in the examples and experiments described below were purchased from Bethesda Research Laboratories, Gainesburg, Md. or New England Biolabs, Beverly, Mass.

The organism, *P.putida* G7, contains a plasmid designated as NAH7 which was the source of DNA for the constructs described below. The NAH7 plasmid is involved in naphthalene degradation and is described in U.S. Pat. No. 4,520,103. The DNA sequence of NAH7 encoding the NDO enzyme system (the nahA gene) was cloned by Ensley et al., *Science*, 222:167 (1983) and subsequently sequenced. About 3500 base pairs (bp) of this DNA sequence encode all of the NDO proteins. The genes encoding these proteins are clustered and sequentially located on the plasmid.

The starting material for the construction of the pACl plasmid was the pCFM526 plasmid. The construction of the pCFM526 plasmid was described in U.S. Pat. No. 4,710,473. The pACl plasmid was derived from pCFM526 by substituting a DNA sequence containing a synthetic $P_L$ promoter and a ribosome binding site between the unique AatII and ClaI restriction sites for the original DNA sequence of pCFM526. The substitution was performed by digesting pCFM526 with AatII and ClaI, isolating the resulting 4000 bp fragment from agarose gel and ligating the fragment with the following oligonucleotide:

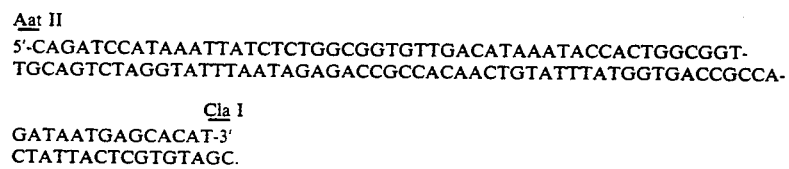

```
     AatII
5'-CAGATCCATAAATTATCTCTGGCGGTGTTGACATAAATACCACTGGCGGT-
   TGCAGTCTAGGTATTTAATAGAGACCGCCACAACTGTATTTATGGTGACCGCCA-

ClaI
GATAATGAGCACAT-3'
CTATTACTCGTGTAGC.
```

The pACl plasmid thus contained a $P_L$ promoter as well as the other sequences of pCFM526 including a heat-inducible promoter, a restriction site bank cloning cluster, a plasmid origin of replication, a transcription terminator, genes regulating plasmid copy number, and a gene conferring ampicillin resistance.

The following procedures were used to isolate and clone the three genes encoding the three polypeptides of the naphthalene dioxygenase enzyme. The gene encoding the ISP polypeptide was a 2500 bp fragment of NAH7 DNA which was isolated and cloned into the publicly available plasmid pUC9 to construct plasmid ISP-pEA2, as shown in FIG. 1. Plasmid ISP-pEA2 was then transformed into *E. coli* strain JM105 as described by Ensley et al., *Microbial Metabolism and the Carbon Cycle*, edited by Hagedorn et al., Harwood Academic Publishers, pp. 437–455 (1988).

The gene encoding the Rd polypeptide of the NDO enzyme system was cloned into pACl by digesting the ProR/Sac plasmid, described below, with XhoI, removing the XhoI/XhoI fragment and religating the plasmid to itself. The resulting construction eliminated about 2200 bp of the ProR/Sac plasmid DNA but retained all of the Rd gene and was designated as Rd-pACl. Plasmid Rd-pACl was also transformed into *E. coli* strain FM5.

In order to prepare a plasmid containing only the Fd gene, the ProR/Sac plasmid was digested with KpnI to eliminate the region containing the ISP gene and the digested plasmid was isolated from an agarose gel. This was followed by a religation step to construct a plasmid designated ProR/Kpn. This construct was digested with ClaI and BamHI to release about a 1500 bp fragment containing both the Rd and the Fd genes. This fragment was further digested with DdeI to generate a 343 bp fragment spanning the DdeI and KpnI restriction sites. The DdeI site is 10 bp upstream of the initiation codon of Fd while the KpnI is 3 bp downstream of the termination codon of Fd. The sticky end of the DdeI site was blunt-ended using S1 nuclease and cloned into a blunt-ended EcoRI site of the pACl plasmid. The KpnI sites of both the Fd gene and pACl were kept intact for proper ligation. This construct containing the Fd gene was designated as Fd-pACl. Plasmid Fd-pACl was transformed into *E. coli* strap in FM5.

The transformed cells were cultured and grown under standard conditions. Shaker flask experiments were performed using 500 ml of Difco Brain Heart Infusion (BHI) broth. Cells were grown to an optical density of 0.5 (600 nm) at 30° C. followed by a three hour incubation period at 42° C. At the end of three hours at 42° C., the incubation was continued at 30° C. for six hours with the addition of indole at a rate of 100 mg/liter/h.

Cell extracts were prepared as described by Ensley et al., *J. Bacteriol.*, 155:505 (1983). Briefly, cells were resuspended (1 g wet weight cells per 2 ml buffer) in 50 mM Tris buffer, pH 7.8, containing 10% glycerol, 10% ethanol and 0.5 mM dithiothreitol (TEG buffer). The cells were disrupted by two passages through a French pressure cell at 7,000 lb/in$^2$ at 4° C. and the resulting mixture was centrifuged for one hour to give a supernatant crude cell extract.

Crude cell extracts prepared from the combined extracts of all three transformed cell lines reconstituted the NDO activity in indole-exposed cells.

The NDO activity of the cell extracts was monitored using a standard procedure. Samples of cells were removed from the growth medium and diluted in Luria broth which gave a cell density measured by absorbance at 550 nm of approximately 0.25. This corresponded to a whole cell protein concentration of approximately 0.05 mg/ml. A 0.5 ml aliquot of the diluted cell suspension was transferred to a small test tube, and the suspension was allowed to equilibrate at room temperature for five minutes. The assay reaction was started by the addition of 50 nmoles of $^{14}$C-naphthalene dissolved in 5 μl of dimethylformamide. The specific activity of the naphthalene was generally between 5,000 and 10,000 counts/min/nmole. The reaction was allowed to proceed for five minutes with occasional vortex mixing. After five minutes, a 20 μl aliquot of the mixture was removed and spotted on a section of a thin layer chromatography plate. Residual naphthalene in the reaction mixture was removed by drying the plate under a stream of air at room temperature for about thirty minutes. The volatile, labelled naphthalene was removed by the stream of air while any naphthalene metabolites produced during the NDO mediated reaction were non-volatile and remained on the plate. The amount of non-volatile $^{14}$C-naphthalene metabolites on the plate were measured by liquid scintillation counting. The assay reaction using radio labelled naphthalene is proportional to the capacity of the enzyme to react with the indole.

Experiments using crude cell extracts from the clones containing isolated NDO polypeptides and those prepared from indole-exposed cells indicated the Fd component to be the most metabolite-limiting polypeptide. This was demonstrated by adding increasing amounts of crude cell extracts, approximately 20 mg/ml of total protein prepared from each clone, to the extract prepared from induced host strain FM5 transformed with all three NDO genes six hours after indole addition. The data compiled in Table 1 indicates there was a 2.5-fold increase in activity with the addition of the Fd polypeptide to the six hour crude extract.

As used herein, the phrase "enhanced naphthalene dioxygenase activity" refers to a time related increase in the naphthalene dioxygenase enzymatic activity of a cell extract produced in a host strain in accordance with this invention as compared to the naphthalene dioxygenase enzymatic activity of a standard cell extract. The comparative standard cell extract is the cell extract of a host strain transformed with a DNA sequence encoding a naphthalene dioxygenase enzyme as described in U.S. Pat. No. 4,520,103.

TABLE 1

NDO ACTIVITY IN 6 HOUR CELLULAR EXTRACT

| NDO Activity (cpm) | Added Rd (μl extract) |
|---|---|
| 4100 | 0 |
| 3500 | 2 |
| 2200 | 6 |
| 1800 | 10 |
| 1750 | 20 |
| | Added Fd (μl extract) |
| 4700 | 0 |
| 8000 | 2 |
| 9800 | 5 |
| 11000 | 10 |
| 11900 | 15 |
| 12500 | 20 |
| | Added ISP (μl extract) |
| 4100 | 0 |
| 5100 | 2 |
| 5000 | 5 |
| 4900 | 10 |
| 5900 | 15 |
| 5800 | 20 |

The following examples are illustrative of particular embodiments of the invention. Example 1 describes adding multiple copies of the Fd gene to a transformed cell. Example 2 describes culturing cells transformed with the NDO genes in the presence of iron. Example 3 describes site selective mutation of the Fd gene.

EXAMPLE 1

The generation of a DNA sequence containing multiple copies of the ferredoxin gene enhanced NDO activity and was constructed using a three step sequence to give the Fd-911 plasmid.

The ProR/SAc plasmid was constructed from the plasmid pN1816. The pN1816 plasmid, shown in FIG. 2, was constructed by initially isolating a 5500 bp PvuII to BglII fragment of NAH7 DNA containing the NDO genes. This fragment was cloned into the HpaI- and BamHI- digested pACl plasmid. In addition to the nahA genes encoding the NDO polypeptides, the 5500 bp fragment of NAH7 DNA contained approximately 800 bp of Pseudomonas DNA upstream from the NDO genes and the nahB gene encoding cis-naphthalene dihydrodiol dehydrogenase downstream from the nahA genes.

Figure 2:
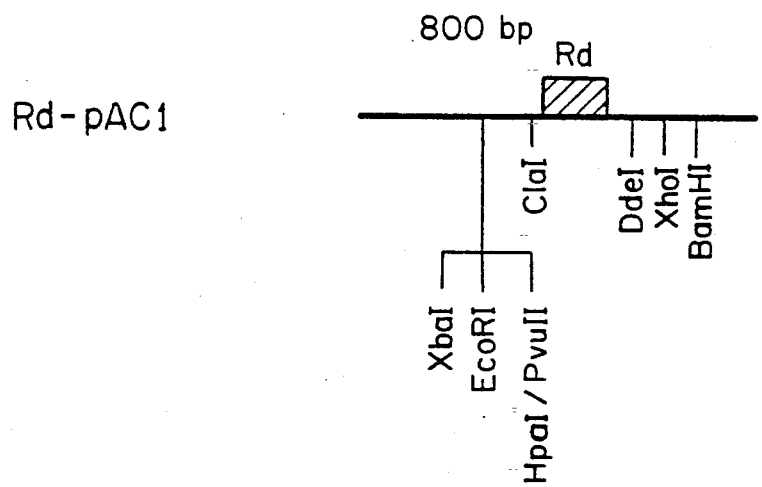
FIG. 2 is a schematic illustration of construct Rd-pAC1.
Figure 3:
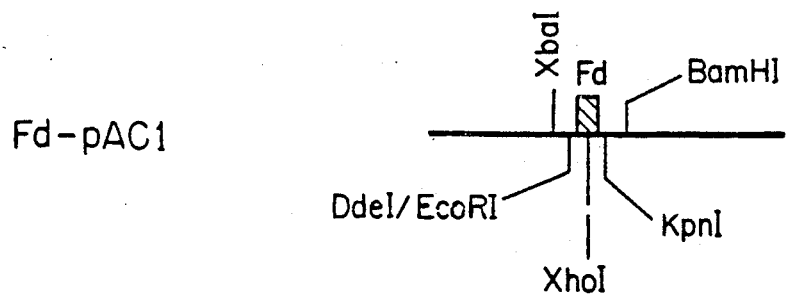
FIG. 3 is a schematic illustration of construct Fd-pACl.

To delete the nahB gene from the pN1816 plasmid, the SacII site located 30 bp downstream from the ISP gene was used to generate the ProR/Sac construct, shown in FIG. 2. The pN1816 plasmid was partially digested with SacII, and the resulting restriction site sticky ends were blunted using Klenow treatment. The DNA was then digested with EcoRI releasing a 4300 bp fragment containing the nahA genes. This 4300 bp DNA fragment was cloned into the pACl plasmid between the EcoRI and HpaI restriction sites creating a plasmid construct designated ProR/Sac.

The ProR/Sac plasmid was transformed into *E. coli* strain FM5, a host organism used for regulation of the P$_L$ expression system. The host organism, FM5, was deposited with the American Type Culture Collection, Rockville, Md. on May 19, 1989 and was designated A.T.C.C. No. 53911.

The next step of the construction required modifying the 5' end of the NDO gene to give the Fd-pACl plasmid. About 800 bp of DNA of unknown function in front of the Rd gene in the ProR/Sac plasmid was deleted to give the 911-pACl plasmid, shown in FIG. 2. A previously constructed plasmid, ATG#6, containing an SstI site in front of the Rd start-site was utilized to design the construct designated 911-pACl.

ATG#6 plasmid was constructed by initially digesting ProR/Sac with EcoRI and HindIII and cloning this fragment into similarly digested and commercially available M13mp11. An SstI site was generated by site-directed mutagenesis at amino acid positions 2 and 3 of the Rd gene without altering the amino acids at these positions. The NAH genes including the mutation were removed from M13mp11 as an approximately 3500 bp fragment by digestion with SstI and HindIII and the SstI/HindIII fragment was cloned into pACl that had been digested with EcoRI and HindIII along with an oligomer linker (AATTCAGGAGGAATAACATATGGAGCTC) having an EcoRI and SstI sticky ends to give the ATG#6 plasmid.

To construct the 911-pACl plasmid, the ATG#6 plasmid was digested with SstI and HindIII and the NAH gene insert removed from M13mp11 was ligated into HindIII and XbaI digested pACl along with the linker (CTAGATGGAGCT) containing XbaI and SstI sticky ends to give the 911-pAcl plasmid.

The synthetic oligomer linker contained the initiation codon of Rd and allowed proper spacing between the Rd gene and the pACl plasmid.

Preparation of Plasmid Fd-911

An additional copy of the Fd gene was inserted in front of the cassette containing all of the NDO genes in the 911-pACl plasmid. This construct was designated as Fd-911, as shown in FIG. 2.

The Fd-pACl plasmid was digested with KpnI and blunted with Klenow treatment. This DNA was further digested with HindIII. The 911-pACl plasmid was first digested with ClaI and blunted with Klenow treatment. The 911-pACl plasmid was further digested with HindIII releasing a 3550 bp DNA fragment containing all four genes. This 3550 bp DNA fragment was isolated by agarose gel electrophoresis and ligated into the KpnI blunted/HindIII digested Fd-pACl plasmid to give the desired gene construct, the Fd-911 plasmid.

The data in Table 2 indicates the result of shaker flask experiments using strain FM5 transformed with the Fd-911 plasmid and shows enhanced NDO activity.

TABLE 2

NDO ACTIVITY WITH PLASMID Fd-911

| NDO Activity (cpm) | Time (hours after heat induction) |
|---|---|
| 5600 | 6 |
| 5700 | 8 |
| 4000 | 10 |
| 2000 | 12 |
| 100 | 21 |

EXAMPLE 2

Addition of Iron to Enhance NDO Activity During Indigo Production

The addition of iron to cell culture broth has been reported to have little stimulating effect on NDO activity, see e.g., Ensley et al., *J. Bacteriol.*, 149:948 (1982). However, iron, by as yet an unknown mechanism, yields a significant effect in increasing the NDO activity during indigo production by the same enzyme.

Based on the results of crude cell extract studies, experiments were initiated to test the effect of iron supplementation on NDO activity using whole cells. Increasing $FeSO_4.7H_2O$ concentrations were tested in BHI medium using *E. coli* FM5 transformed with ProR/Sac as the production strain. Results obtained from shaker flask experiments, in which the medium was supplemented with iron confirmed this observation. The data shown in Table 3 indicates higher concentrations of $FeSO_4.7H_2O$ increased NDO activity in cell extracts.

TABLE 3

NDO ACTIVITY IN CELL EXTRACTS

| | NDO Activity (cpm) | Time (hours after heat induction) |
|---|---|---|
| NO IRON | 2000 | 6 |
| | 1000 | 8 |
| | 400 | 11 |
| ADDED IRON | 2100 | 6 |
| | 2000 | 8 |
| | 1800 | 11 |

The data in Table 3 indicates NDO activity typically decreases both after indole feed and during indigo production. However, supplementing the crude cell extract with 0.3 $\mu$mol $FeSO_4.7H_2O$ maintained the NDO activity in both the 8 and 11 hour crude extracts to nearly normal levels.

Table 4 indicates the approximate saturating levels of added $FeSO_4.7H_2O$. A total of 1.8 g/l or 3.6 g/l of $FeSO_4.7H_2O$ was added with 0.6 g/l of indole over a 6 hour period following induction. Approximately 70% and 50% of the original activity remained after 6 and 10 hours following indole feed, respectively.

TABLE 4

NDO ACTIVITY WITH PLASMID ProR/Sac and IRON

| | NDO Activity (cpm) | Time (hours after heat induction) |
|---|---|---|
| NO $FeSO_4.7H_2O$ | 9000 | 6 |
| | 5000 | 8 |
| | 2000 | 10 |
| | 1750 | 12 |
| | 200 | 21 |
| 1.8 g/l $FeSO_4.7H_2O$ | 9000 | 6 |
| | 12000 | 8 |
| | 9100 | 10 |
| | 6300 | 12 |
| | 200 | 21 |
| 3.6 g/l $FeSO_4.7H_2O$ | 9000 | 6 |
| | 12000 | 8 |
| | 9100 | 10 |
| | 6200 | 12 |
| | 200 | 21 |

Additional experiments also showed the NDO activity may be enhanced by adding iron to the culture broth used to grow cells transformed with a DNA sequence encoding an extra copy of the Fd gene, exemplified by the Fd-911 plasmid, and to grow cells transformed with a DNA sequence encoding a ferredoxin analog, as exemplified by the Fd-911ABC plasmid. When the BHI medium was supplemented with iron during indole feed, NDO activity was retained for extended periods. The supporting data is compiled in Table 5.

The results of the experiments in this example show NDO activity may be significantly enhanced by the addition of iron to the crude extracts or to the growth medium.

TABLE 5

NDO ACTIVITY WITH PLASMID Fd-pAClABC and Fd-911

| | NDO Activity (cpm) | Time (hours after heat induction) |
|---|---|---|
| plasmid Fd-911ABC and 1.8 g/l FeSO$_4$.7H$_2$O | 8000 | 6 |
| | 11000 | 8 |
| | 12000 | 10 |
| | 12250 | 12 |
| | 1800 | 21 |
| plasmid Fd-911 and 1.8 g/l FeSO$_4$.7H$_2$O | 5600 | 6 |
| | 8000 | 8 |
| | 9250 | 10 |
| | 8000 | 12 |
| | 3750 | 21 |

EXAMPLE 3

A ferredoxin gene derivative modified by site-directed mutation also enhanced NDO activity. The change in the amino acid sequence at position 47 from His to Cys made this position in consensus with about 23 other ferredoxin sequences reported in the literature. The change in the amino acid sequence at position 52 from Met to Ile eliminated the sulfur group found in the Met while keeping the charge at that position similar to the naturally occurring amino acid. The change in the amino acid sequence at position 67 from His to Arg eliminated the His at this position and replaced it with an amino acid having similar properties. These changes in the ferredoxin polypeptide resulted in increased NDO activity.

Site-directed Mutagenesis of the Fd Gene

The Fd gene was changed to give different amino acids in the amino acid sequence at positions 47, 52, and 67. These changes were His to Cys, Met to Ile and His to Arg, respectively. The oligomers used to make these mutations are shown below. Site-specific changes are underlined.

| Oligomer | Amino Acid Change | Gene Designation |
|---|---|---|
| CCTGTGCACG<u>T</u>GTGGTGCCGC | His→Cys | A |
| CCGCAT<u>C</u>AGCGATGGTTATCTC | Met→Ile | B |
| TCGCCCTTGC<u>G</u>TCAAGGTCGG | His→Arg | C |

The Fd-pACl plasmid was digested with XbaI and HindIII and the resulting 345 bp fragment was cloned into plasmid M13mp11, commercially available from New England Biolabs, Beverly, Mass. The changes to the three DNA sequences by site-directed mutagenesis were performed by essentially following known procedures described in *Current Protocols in Molecular Biology*, edited by Ausubel et al., Greene Publishing Associates and Wiley Interscience, chapter 8 (1987). After mutagenesis, the mutated Fd gene was removed from the M13mp11 plasmid by digestion with XbaI and HindIII sites. This mutated Fd gene was cloned into the pACl plasmid digested with XbaI and HindIII to give the new plasmid, Fd-pAClABC. The Fd-pAClABC plasmid was then treated as described above in the construction of the Fd-911 plasmid to construct a plasmid designated Fd-911ABC. The data showing extended NDO activity in a strain carrying the Fd-911ABC plasmid is compiled in Table 5, discussed above.

While the present invention has been described in terms of specific methods and compositions, it is understood that variations and modifications will occur to those skilled in the art upon consideration of the present invention.

Accordingly, it is intended in the appended claims to cover all such equivalent variations which come within the scope of the invention as claimed.

We claim:

1. A process for enhancing naphthalene dioxygenase activity to produce indigo from indole in an organism comprising the step of:
   transforming a microorganism with a DNA sequence encoding at least two naphthalene dioxygenase ferredoxin polypeptides for each naphthalene dioxygenase reductase polypeptide and iron-sulfur polypeptide, wherein said microorganism has DNA sequences that express a naphthalene dioxygenase enzyme which comprises reductase, ferredoxin and iron-sulfur polypeptides.

2. The process as recited in claim 1 further comprising the step of:
   growing said transformed microorganism in a culture broth containing an amount of iron effective to enhance said naphthalene dioxygenase activity to produce indigo from indole.

3. The process as recited in claim 1 further comprising the step of:
   transforming said microorganism with a DNA sequence encoding a naphthalene dioxygenase ferredoxin analog having Cys at position 47, Ile at position 52 and Arg at position 67 in said naphthalene dioxygenase ferredoxin analog amino acid sequence.

4. The process as recited in claim 3 further comprising the step of:
   growing said microorganism in a culture broth containing an amount of iron effective to enhance said naphthalene dioxygenase activity to produce indigo from indole.

5. A process for enhancing naphthalene dioxygenase activity in a microorganism comprising the step of:
   growing microorganism in a culture broth containing an amount of iron effective to enhance said naphthalene dioxygenase activity to produce indigo from indole, wherein said organism has DNA sequences that express a naphthalene dioxygenase enzyme which comprises reductase, ferredoxin and iron-sulfur polypeptides.

6. The process as recited in claim 5 wherein said amount of iron is from about 1.8 to 3.6 g/l of FeSO$_4$.7H$_2$O.

7. A process for enhancing naphthalene dioxygenase activity to produce indigo from indole in an organism comprising the step of:
   transforming a microorganism with a DNA sequence encoding a naphthalene dioxygenase ferredoxin analog having Cys at position 47, Ile at position 52 and Arg at position 67 in said naphthalene dioxygenase ferredoxin analog amino acid sequence, wherein said microorganism has DNA sequences that express a naphthalene dioxygenase enzyme which comprises reductase, ferredoxin and iron-sulfur polypeptides.

8. A DNA sequence encoding a naphthalene dioxygenase ferredoxin analog having Cys at position 47, Ile at position 52 and Arg at position 67 in said naphthalene dioxygenase ferredoxin analog amino acid sequence.

9. A plasmid comprising:
a DNA sequence encoding a naphthalene dioxygenase ferredoxin analog having Cys at position 47, Ile at position 52 and Arg at position 67 in said naphthalene dioxygenase ferredoxin analog amino acid sequence.

10. The plasmid as recited in claim 9 wherein said plasmid is selected from the group consisting of Fd-911ABC and Fd-pAC1ABC.

11. A host cell comprising a DNA sequence encoding a naphthalene dioxygenase ferredoxin analog having Cys at position 47, Ile at position 52 and Arg at position 67 in said naphthalene dioxygenase ferredoxin analog amino acid sequence.

12. A plasmid comprising:
a DNA sequence encoding at least two naphthalene dioxygenase ferredoxin polypeptides for each naphthalene dioxygenase reductase polypeptide and iron-sulfur polypeptide.

13. A plasmid as recited in claim 12 wherein said plasmid in Fd-911.

14. A host cell comprising:
a DNA sequence encoding at least two naphthalene dioxygenase ferredoxin polypeptides for each naphthalene dioxygenase reductase polypeptide and iron-sulfur polypeptide.

15. A process for enhancing naphthalene dioxygenase activity to microbially produce indigo from indole comprising:
growing a microorganism in a culture broth containing an amount of iron effective to enhance said naphthalene dioxygenase activity to produce indigo from indole, wherein said microorganism is transformed with *Pseudomonas putida* DNA sequences encoding a naphthalene dioxygenase enzyme.

16. A process for enhancing naphthalene dioxygenase activity to microbially produce indigo from indole comprising:
transforming a microorganism with a modified *Pseudomonas putida* DNA sequence encoding at least two naphthalene dioxygenase ferredoxin polypeptides for each naphthalene dioxygenase reductase polypeptide and iron-sulfur polypeptide.

17. A process for enhancing naphthalene dioxygenase activity to microbially produce indigo from indole comprising:
transforming a microorganism with a modified *Pseudomonas putida* DNA sequence encoding naphthalene dioxygenase ferredoxin analog having Cys at position 47, Ile at position 52 and Arg at position 67 in said naphthalene dioxygenase ferredoxin analog amino acid sequence, reductase and iron-sulfur polypeptides.

* * * * *

UNITED STATES PATENT AND TRADEMARK OFFICE
CERTIFICATE OF CORRECTION

PATENT NO. : 5,173,425
DATED : December 22, 1992
INVENTOR(S) : Serdar et al.

It is certified that error appears in the above-identified patent and that said Letters Patent is hereby corrected as shown below:

```
On the title page, Item [21]: "289,738" should be --389,738--.
On the title page, Col. 2, line 1, "Dioxygnase" should be --
     Dioxygenase--.
```

Col. 6, line 37, "2" should be -- 4--.

Col. 6, line 50, "2" should be -- 5--.

Col. 6, line 68, "2" should be --6--.

Col. 7, line 32, "2" should be --7--.

Col. 10, line 13, "organism" should be --microorganism--.

Col. 10, line 45, insert --a-- after "growing".

Col. 10, line 48, "organism" should be --microorganism--.

Col. 10, line 56, "an organism" should be --a microorganism--.

Signed and Sealed this

Fifteenth Day of September, 1998

Attest:

BRUCE LEHMAN

*Attesting Officer*   *Commissioner of Patents and Trademarks*